United States Patent
Trent

(10) Patent No.: US 9,005,584 B2
(45) Date of Patent: Apr. 14, 2015

(54) SPRAY FORMULATIONS WITH REDUCED CLOGGING/SEDIMENTATION CHARACTERISTICS

(75) Inventor: John S. Trent, Franklin, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 209 days.

(21) Appl. No.: 13/492,007

(22) Filed: Jun. 8, 2012

(65) Prior Publication Data

US 2013/0330282 A1  Dec. 12, 2013

(51) Int. Cl.
*A61K 9/12* (2006.01)
*A01N 25/00* (2006.01)
*A61K 8/73* (2006.01)
*A61K 8/19* (2006.01)

(52) U.S. Cl.
CPC .. *A61K 8/732* (2013.01); *A61K 8/19* (2013.01)

(58) Field of Classification Search
None
See application file for complete search history.

(56) References Cited

U.S. PATENT DOCUMENTS

| | | | |
|---|---|---|---|
| 5,575,988 A * | 11/1996 | Knowles et al. | 424/59 |
| 5,711,797 A | 1/1998 | Ettlinger et al. | |
| 6,488,949 B2 | 12/2002 | Shafer et al. | |
| 6,581,807 B1 | 6/2003 | Mekata | |
| 6,833,185 B2 | 12/2004 | Zhu et al. | |
| 7,189,387 B2 | 3/2007 | Chuah et al. | |
| 7,244,416 B2 | 7/2007 | Meyer et al. | |
| 7,531,187 B2 | 5/2009 | Jadhav et al. | |
| 2004/0081629 A1 | 4/2004 | Meyer et al. | |
| 2004/0120905 A1 | 6/2004 | Gall et al. | |
| 2005/0244443 A1 * | 11/2005 | Stiller et al. | 424/401 |
| 2008/0213192 A1 | 9/2008 | Schlesinger et al. | |
| 2009/0189090 A1 | 7/2009 | Meyer et al. | |

FOREIGN PATENT DOCUMENTS

| | | |
|---|---|---|
| EP | 1291301 A1 | 3/2003 |
| GB | 2113116 A | 8/1983 |
| WO | WO80/02293 A1 | 10/1980 |
| WO | WO94/09626 | 5/1994 |
| WO | WO2007/133638 A2 | 11/2007 |

OTHER PUBLICATIONS

International Search Report and Written Opinion, PCT/US213/044281, Date of Mailing: Oct. 11, 2013.

* cited by examiner

*Primary Examiner* — Carlos Azpuru
*Assistant Examiner* — Casey Hagopian

(57) ABSTRACT

Spray compositions are formulated with powders (e.g. corn starch) which improve skin feel, and also have a hydrophobically modified oxide additive (e.g. modified silica) to reduce the incidence of can/bottle clogging and sedimentation caused by the powder. The oxide is a mixed hydrophobic/hydrophilic oxide such as hydrophobicly modified fumed silica (e.g. silica dimethyl silylate). In one embodiment DEET can be delivered by such formulations.

20 Claims, No Drawings

SPRAY FORMULATIONS WITH REDUCED CLOGGING/SEDIMENTATION CHARACTERISTICS

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to spray formulations. It is particularly well suited for application to insect repellent aerosol formulations that provide improved skin feel without unacceptably increasing the risk of clogging or undesired sedimentation.

A variety of formulations have been developed for spraying on human skin which are designed to be sprayed from an aerosol can or a pump sprayer. For example, a typical insect repellent spray formulation contains an insect repellent, a carrier solvent, a propellant gas (in the case of an aerosol spray), and minor amounts of other materials (e.g. fragrance, corrosion inhibitor and emollient).

Attempts have been made to add powdery materials (particularly corn starch) to such formulations so that the resulting spray has a smooth/dry feel on the skin. See generally U.S. Pat. No. 6,581,807. Unfortunately, powders such as starches tend to cake in aerosol cans when included in formulations of this type, and then form chunks that do not disperse easily even with shaking of the can/bottle prior to each use. This can clog the delivery tube and nozzle of the spraying device and cause unwanted sedimentation (which reduces the powder concentration in the delivered spray even when there is no clogging).

Complicating matters further is that any ingredient added to such a formulation must be suitable for the use on skin and adjacent clothing. Further, the ingredient must be compatible with other conventional spray formulation ingredients during long term storage. This has made resolving these concerns a challenging problem.

Thus, a need still exists to find ways to deliver spray formulations (particularly insect repellent aerosol spray formulations) having a smooth/dry skin feel, while avoiding clogging and sedimentation problems, and while maintaining repellency characteristics of the spray.

BRIEF SUMMARY OF THE INVENTION

In one aspect the invention provides a spray formulation that includes starch, water, a carrier, and an oxide selected from the group consisting of silicon oxide, titanium oxide, and aluminum oxide, where the oxide has been modified to have a hydrophobic portion even though the oxide also has a hydrophilic portion. Most preferably the oxide is silicon oxide in the form of fumed silica which has been modified to have a hydrophobic surface portion (even though also having a hydrophilic surface portion). For example, the hydrophilic portion may be a remaining surface hydroxyl group, and the hydrophobic portion may have been formed by reacting another hydroxyl portion of hydrophilic fumed silica with a silane (e.g. dimethyldichlorosilane; trimethoxyoctylsilane; hexamethyldisilazane) to form a silica alkyl silylate or with a siloxane (e.g. polydimethylsiloxane; octamethylcyclotetrasiloxane) to form another hydrophobic moiety.

The carrier may be selected from the group consisting of alcohol solvents (e.g. ethanol) and gas propellants (e.g. a hydrocarbon such as butane or propane). If desired there may be more than 10% by weight of an alcohol solvent and more than 30% by weight of the gas propellant, in a formulation that is an aerosol formulation.

Especially preferred is particulate corn starch in an amount of at least 5% by weight, used with 0.1% or more by weight of the modified oxide. The particle size of the starch should preferably be greater than an average particle size of the oxide (e.g. several times greater in size, and more preferably more than nine times greater in average size).

An initial application for this technology is in connection with insect control agents sprayed on human skin. For example, an insect repellent and/or insecticide such as DEET (N,N-diethyl-meta-toluamide) can be applied in a formulation with at least 5% (more preferably at least 15%) by weight DEET.

More precise control over skin feel can be achieved by also adding in another powder such as magnesium carbonate (e.g. about 2% by weight). Further, other desired skin treatment materials may be added such as emollients selected from the group consisting of isopropyl myristate and silicone fluid. In a particularly preferred form one may use about 25% ethyl alcohol, a few percent isopropyl myristate, and about 0.1% silicone fluid.

It is preferred to use an Aerosil® hydrophobic fumed silica, available from Evonik Industries, such as R 974, R972, R8200, R8125, R812, R805, or R202. Most preferred is R974 given its nanoscale particle size and mix of hydrophobic and hydrophilic properties. It is believed that there are advantages to having a carbon content in the modified oxide of between 0.1 and 5 weight % (preferably less than 2%), considering the mixed water and hydrocarbon environment.

Analogous modifications can be made to titanium oxide and/or aluminum oxide materials, with the fumed silica being replaced with the corresponding titanium oxide or aluminum oxide. For example, one can use Aeroxide® $TiO_2$ T805 from Evonik (which has fumed titanium dioxide rendered more hydrophobic by reacting it with an octylsilane), or Aeroxide® Alu C 805 from Evonik (which has fumed aluminum oxide rendered more hydrophobic by reacting it with an octylsilane).

Preferred modified oxide surface areas are between 25 and 300 $m^2/g$.

For aerosol formulations a wide variety of gas propellants can be used such as hydrocarbon propellants (particularly butane/propane mixes such as B-52 propellant).

While the initial formulations used corn starch, other starch containing materials can replace the corn starch such as those derived from rice, silk, tapioca, allantoin or arrowroot.

While the invention was initially developed for DEET formulations, it appears suitable for use with a wide variety of other insect repellents, insecticides, and insect growth regulators. Of course where the materials are to be applied directly to human skin, insect control agents suitable for skin contact should be selected.

If desired, insect control formulations may also contain fragrances mixed into them. Alternatively, a perfume fragrance may be applied to the skin by replacing the insect control ingredient with a perfume.

Without limiting the claim scope to any particular theory of operability, it is believed that the oxides of the present invention coat the starch, thereby inhibiting the tendency for caking/clogging/forming sediment in the can/bottle. The mixed hydrophobic/hydrophilic nature of the oxides allows a reversible gel network to form in a mixed aqueous/hydrocarbon environment. Yet, this does not frustrate the ability of the starch/magnesium carbonate to provide a dry/smooth feel.

In sum, using the present invention, clogging and sedimentation effects are reduced, while the smooth/dry skin feel (and insecticidal utility) are maintained.

The foregoing and other advantages of the present invention will be apparent from the following description. As these embodiments are merely illustrative, they are not intended to represent the full scope of the invention. Thus, reference should therefore be made to the claims herein for interpreting the scope of the invention.

DETAILED DESCRIPTION OF THE PREFERRED EMBODIMENTS

For purposes of this patent, the "insect" is being used in a broad sense to not only mean conventional six-legged insects, but also to cover other pests typically controlled along with insects (such as arachnids). Also, for purposes of this application the term "control" means to affect the insect in a manner desired by the user, including for example repelling, killing, or knocking down.

Various formulations were prepared and evaluated. These formulations had between about 30 to 40% of a hydrocarbon propellant gas (butane or a butane/propane mix), between about 20 to 28% of ethyl alcohol, between about 15 to 26% of DEET, between about 10 to 12% of corn starch, between about 4 to 5% deionized water, about 0.7% fragrance, about 0.25% of a corrosion inhibitor such as sodium benzoate and/or 2-amino-2-methyl-1-propanol, about 1.5% to 5% of an emollient such as isopropyl myristate and/or silicone, about 1.5 to 2% of magnesium carbonate, and about 0.15 to 0.6% of a hydrophobic fumed silica (e.g. Aerosil R974). One pump spray formulation could be the same as one the above aerosol formulations, but with the gas left out.

It was then tested how quickly powder would settle out of these formulations in a non-agitated environment, the powder height in the container over time, re-suspension rates in an inversion test, spray testing while monitoring for clogging, and (for some formulations) dryness feel. By increasing the concentration of (for example) R974 from 0% to 0.6% a marked improvement in sedimentation characteristics was noticed. Compounds of the present invention (in standard spray cans) also exhibited marked improvement insofar as reducing spray clogging and sedimentation.

Hence, by including these hydrophobically modified oxides one can achieve reduced clogging and sedimentation, without materially compromising skin feel or other desired characteristics. Moreover, the oxides appear compatible with standard formulations and suitable for use in a skin environment.

While the preferred embodiments of the present invention have been described above, it should be appreciated that there are other embodiments within the spirit and intended scope of this disclosure. For example, instead of using R974, one can use other fumed silicas that have different modified hydroxyl groups, or different proportions of hydroxyl groups to modify hydroxyl groups. An example is to use a longer alkyl group instead of methyl by reacting the silica with an octasilane, or use only a single alkyl group, rather than two, per silicon. Alternatively, one can react the silica with a siloxane. Reference should be made to the Evonik lines of Aerosil® and Aeroxide® products for additional alternatives.

These and still other modifications are meant to be within the scope of the invention. Thus, the invention is not to be limited to just the specific embodiments shown or described.

INDUSTRIAL APPLICABILITY

Provided herein are improved spray formulations, such as those that provide improved skin feel when contacted by a consumer (without causing unacceptable clogging and/or sedimentation, or unacceptably undermining insect control).

All documents cited in this document are, in relevant part, incorporated herein by reference. The citation of any document is not to be construed as an admission that it is prior art with respect to the present invention.

What is claimed is:

1. An aerosol spray formulation, comprising:
   starch;
   water;
   a carrier; and
   an oxide selected from the group consisting of silicon oxide, titanium oxide, and aluminum oxide, where the oxide has been modified to have a hydrophobic portion even though the oxide also has a hydrophilic portion,
   wherein the starch is in particulate form and an average particle size of the starch is greater than an average particle size of the oxide.

2. The aerosol spray formulation of claim 1, wherein the modified oxide is silicon oxide in the form of fumed silica which has been modified to have a hydrophobic portion while also having a hydrophilic portion.

3. The aerosol spray formulation of claim 1, wherein the hydrophilic portion comprises a hydroxyl group.

4. The aerosol spray formulation of claim 1, wherein the hydrophobic portion was formed by treating a portion of hydrophilic fumed silica with a silane or siloxane.

5. The aerosol spray formulation of claim 4, wherein the oxide comprises a silica alkyl silylate hydrophobic portion.

6. The aerosol spray formulation of claim 5, wherein the oxide comprises a silica dimethyl silylate hydrophobic portion.

7. The aerosol spray formulation of claim 1, wherein the carrier is selected from the group consisting of alcohol solvents and gas propellants.

8. The aerosol spray formulation of claim 7, further comprising at least 10% by weight of an alcohol solvent.

9. The aerosol spray formulation of claim 7, wherein the carrier comprises a hydrocarbon gas propellant.

10. The aerosol spray formulation of claim 1, wherein the starch is corn starch.

11. The aerosol spray formulation of claim 1, wherein the formulation comprises at least 0.1% by weight of the modified oxide.

12. The aerosol spray formulation of claim 1, further comprising an ingredient selected from the group consisting of insect control agents and fragrances.

13. The aerosol spray formulation of claim 12, wherein the ingredient is an insect control agent and is selected from the group consisting of insect repellents and insecticides.

14. The aerosol spray formulation of claim 12, wherein the insect control agent is N,N-diethyl-meta-toluamide.

15. The aerosol spray formulation of claim 1, further comprising magnesium carbonate.

16. The aerosol spray formulation of claim 1, further comprising an emollient selected from the group consisting of isopropyl myristate and silicone fluid.

17. The aerosol spray formulation of claim 1, wherein the modified oxide has a carbon content of between 0.1% and 5% by weight.

18. A spray formulation, comprising:
   starch;
   water;
   a carrier;
   magnesium carbonate; and
   an oxide selected from the group consisting of silicon oxide, titanium oxide, and aluminum oxide where the oxide has been modified to have a hydrophobic portion even though the oxide also has a hydrophilic portion.

19. A spray formulation, comprising:
   corn starch;
   water;
   a carrier; and
   an oxide selected from the group consisting of silicon oxide, titanium oxide, and aluminum oxide, where the oxide has been modified to have a hydrophobic portion even though the oxide also has a hydrophilic portion.

20. The spray formulation of claim 19, wherein the formulation comprises at least 5% by weight corn starch, and the formulation is an aerosol formulation.

\* \* \* \* \*